United States Patent [19]
Sendelsky et al.

[11] Patent Number: 5,929,282
[45] Date of Patent: Jul. 27, 1999

[54] SYSTEM AND METHOD FOR DISPOSAL OF HYDRAZINE PROPELLANTS AND OTHER ENERGETIC MATERIALS

[75] Inventors: Ken Sendelsky, Chester; Brent S. DeFeo, Sparta, both of N.J.; Russell W. Johnson, Elmhurst, Ill.; Subramaniam E. Haran, Morris Plains, N.J.; Alexander M. Bershitsky, Chicago; Martin Andren, Lake in the Hills, both of Ill.; John Yamanis, Morristown, N.J.

[73] Assignee: AlliedSignal Inc., Morristown, N.J.

[21] Appl. No.: 09/039,547

[22] Filed: Mar. 16, 1998

Related U.S. Application Data

[60] Provisional application No. 60/039,090, Mar. 17, 1997.

[51] Int. Cl.$^6$ ............................. C01C 1/00; C07C 211/00
[52] U.S. Cl. ............................. 564/423; 423/352
[58] Field of Search ............................. 524/463; 423/352

[56] References Cited

U.S. PATENT DOCUMENTS

| | | | |
|---|---|---|---|
| 4,122,671 | 10/1978 | Armstrong et al. | 60/218 |
| 4,661,179 | 4/1987 | Hunter et al. | 149/124 |
| 5,437,853 | 8/1995 | Johnson et al. | 423/352 |

*Primary Examiner*—Brian M. Burn
*Attorney, Agent, or Firm*—Riker, Danzig, Scherer, Hyland and Perretti; Ernest D. Buff; Leslie G. Restaino

[57] ABSTRACT

An apparatus and method for converting hydrazine, substituted hydrazines and/or other nitrogen-containing explosive materials, particularly unsymmetric dimethyl hydrazine (UDMH), to ammonia or ammonia and the corresponding amines by hydrogenation are disclosed. The hydrazines are diluted with a suitable carrier fluid, preferably water, mixed with hydrogen, then hydrogenated in a catalyst reactor, followed by separation of the commercially valuable ammonia and amines. Separated carrier fluid and hydrogen gas may be recycled in to the process to conserve energy and reduce waste. Recycled carrier fluid may be used to preheat the diluted hydrazine prior to hydrogenation. Ammonia may be dissociated and the resultant hydrogen recycled into the hydrogenation process. The apparatus is sized for disassembly and transport for shipping to hydrazine disposal sites.

22 Claims, 4 Drawing Sheets

5,929,282

SYSTEM AND METHOD FOR DISPOSAL OF HYDRAZINE PROPELLANTS AND OTHER ENERGETIC MATERIALS

CROSS REFERENCE TO RELATED APPLICATIONS

This application claims the benefit of U.S. Provisional Application No. 60/039,090, filed Mar. 17, 1997.

BACKGROUND OF THE INVENTION

1. Field of the Invention

The present invention relates to the disposal of energetic materials; and more particularly to system configurations and methods for using the same to deactivate hydrazines, such as unsymmetric dimethyl hydrazine (UDMH), which are used as propellants, and convert such hazardous charge stock into valuable end products, including diethylamine and ammonia.

2. Description of the Prior Art

Large quantities of energetic materials, for example, hydrazine, substituted hydrazines such as alkyl hydrazines, and other nitrogen-containing explosive materials, have been produced worldwide for use as rocket propellants and other forms of explosives. The need to deactivate rockets utilizing these propellants, particularly in a post cold war society, as well as other weapons and processes that produce or utilize nitrogen-containing explosives, has been a growing concern. Although disposal of energetic materials by means of incineration is known, the resultant waste products such as carbon dioxide and oxides of nitrogen are undesirable pollutants that need to be controlled. For example, the incineration of unsymmetrical dimethyl hydrazine (UDMH), a liquid rocket fuel, results in the formation of carbon dioxide, nitrogen, water, and various oxides of nitrogen according to the following reaction:

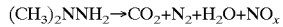
$(CH_3)_2NNH_2 \rightarrow CO_2+N_2+H_2O+NO_x$

Disposal of waste energetic materials would also be most beneficial if the resultant products of the disposal method had commercial value.

Catalytic hydrotreating is a proven method for the conversation of hazardous materials and the recovery of valuable resources. For example, large-scale application of catalytic hydrotreating is used to remove oxygen-, nitrogen-, and sulfur-containing contaminants from many petroleum fractions by converting the fractions into water, ammonia, hydrogen sulfide and hydrocarbons. Catalytic hydrotreating technology can be used for the catalytic destruction of a wide range of hazardous materials that include waste hydrocarbons, explosives, propellants, and halogenated waste streams, and is an attractive alternative to incineration.

For example, it has been known that substituted hydrazines can be hydrogenated to ammonia and amines utilizing various catalysts, especially noble metal catalysts, discussed in U.S. Pat. No. 5,437,853. However, the '853 patent is directed to a method of hydrotreating, and contains little if any teaching of apparatus configurations to accomplish large scale catalytic hydrotreating of hydrazine safely, effectively and efficiently.

SUMMARY OF THE INVENTION

The present invention provides a method and means for disposing of hydrazine and related energetic materials in a system having the least adverse impact on the environment. Advantageously, disposal of hydrazine and related energetic materials is accomplished while at the same time producing valuable by-products.

More specifically, the invention is directed to a chemical plant and method for the catalytic hydrotreating of a wide range of hazardous materials that include waste hydrocarbons, explosives, propellants, and halogenated waste streams, while allowing for the recovery of commercially valuable by-products and waste. The system according to the present invention is a modular combination of mixing tanks, reactors and separation tanks, assembled in a closed-loop configuration, such that catalytic hydrotreating of hazardous materials or other feedstock occurs in a controlled and safe manner. The resultant by-products are collected, and either recycled to completion of the process or removed from the process for use elsewhere.

The chemical plant of the present invention comprises a series of stages beginning when a liquid or gaseous feedstock is introduced into the plant. The feedstock is diluted or mixed with a carrier, mixed with hydrogen gas, catalytically hydrotreated, and separated by product types. Some of the products may be recycled within the plant for further reaction with the feedstock.

In one embodiment, the chemical plant is configured for the catalytic hydrotreating of unsymmetric dimethyl hydrazine (UDMH) into ammonia and dimethyl amine, according to the following chemical equation:

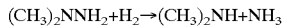
$(CH_3)_2NNH_2+H_2 \rightarrow (CH_3)_2NH+NH_3$

Upon introduction into the plant, the UDMH feedstock is diluted and dissolved with a suitable liquid carrier, preferably water, and transferred to a holding tank. The solvent serves to moderate the effect of the exothermic heat of reaction that occurs during hydrotreating, resulting in a cooler, and safer, system. When available, products for recycling may also be introduced into the diluted feedstock. This diluted UDMH is then mixed with hydrogen gas, the combination heated and introduced into a catalytic reactor. Effluent from the reactor is introduced into a first separation tank, where the liquid effluent is tapped and routed to a first distillation column. The gaseous effluent, containing primarily hydrogen gas, is tapped from the first separation tank and routed to a scrubber unit. In the scrubber, compounds such as ammonia and dimethylamines are removed so as not to contribute to the formation of NOx later when these gases are utilized in the boiler, minimizing the use of more costly hydrogen gas from an outside source. The off gases from the scrubber unit are routed to an off gas converter reactor where any feedstock remaining in the stream is converted, the reactor acting as a guard bed to insure that none of the feedstock is conducted to the boiler operation and prevent the formation of toxic nitrosamines. Liquid effluent from the scrubber is charged to the first distillation column in order to remove any ammonia, dimethylamines and other basic compounds resulting from the scrubbing action. The resulting distillate from the first distillation column is transferred to a second separation tank. The second separation tank is a reflux drum to the first distillation column. The composition of the material entering this reflux drum may be analyzed with in-line analytical equipment, however the flow is generally predetermined to result in an optimum reflux ratio. That is, the flow is analyzed to determine if the reflux ratio is optimum. For example, if the reflux ratio is 6, 6 volumes of liquid condensed in the reflux drum (separation tank 2) are returned to the top of the first distillation column for every 1 volume of overhead allowed to continue in flow to a second distillation column. The reflux ration may range from approximately 2 to infinity, where infinity permits the complete reflux, the best mode for operation is a reflux ration between approximately 4 and 8. Bottoms from the first column contain mostly water which is recovered and may be returned for mixing with the undiluted feedstock.

The resultant distillate from the second column is routed to a third separation tank. The third separation tank is a reflux drum to the second distillation column. The liquid collected in the second reflux drum is either refluxed to the second column in a manner similar to the refluxing at the first distillation column, or routed to a first product tank. The contents of the first product tank, mostly ammonia, can be stored or treated further, while off-specification ammonia can be advantageously returned to either the first or second distillation column for reprocessing to completion, or to a third product tank containing only off-specification materials for use elsewhere. The effluent from the second column, containing mostly dimethyl amine (DMA), is routed to a second product tank. Off-specification DMA can advantageously be returned to either the first or second column for reprocessing, or to a third product tank containing only off-specification materials for use elsewhere.

In a second embodiment, the ammonia collected in the first product tank is routed to an ammonia dissociator system, where the ammonia is dissociated into hydrogen and nitrogen, utilizing an alumina catalyst according to the following equation:

$$NH_3 \rightarrow \tfrac{1}{2}N_2 + 3/2 H_2$$

Other catalysts may be utilized, including Fe/Ni.

The resulting hydrogen gas can be recycled and introduced as part of the make-up hydrogen introduced to the diluted feedstock prior to introduction of the diluted feedstock into the hydrotreating reactor. The generation of hydrogen from the product ammonia, and the return of this hydrogen back into the system, results in cost savings since hydrogen does not have to be supplied from other more expensive sources. Additionally, the generated hydrogen not recycled and introduced as part of the make-up hydrogen for introduction to the diluted feedstock can be utilized within the system as fuel gas used to supply a portion of the required energy for the reactors and rectifiers throughout the system. Under nominal closed loop operating conditions this invention utilizes approximately two-thirds of the generated hydrogen to react with the diluted feedstock, and remaining one-third available for fuel gas. Additionally, this invention may be operated in open loop as known in the art, and various percentages of hydrogen may be used or recycled depending on the feedstock.

In another embodiment, impurities in the process ammonia, which may be up to 0–5 wt. % dimethyl amine along with similar levels of trimethyl and monomethyl amines, can be dissociated to methane and nitrogen using a suitable catalyst such as nickel, which may be on a ceramic support such as alumina, according to the following chemical reaction in a second reactor:

$$(CH_3)_2NH + 2H_2 \rightarrow 2CH_4 + NH_3$$

The resultant ammonia may then be converted into hydrogen in a third reactor according to the following reaction:

$$NH_3 \rightarrow \tfrac{1}{2}N_2 + 1\tfrac{1}{2}H_2$$

The conversation of the amines to methane advantageously promotes stability of the ammonia dissociation and prevents coking from occurring in the reactors.

In another embodiment, the warm bottoms from a separation column, when recycled and mixed with the feedstock, is first passed through a heat exchanger in order to heat the feedstock prior to introduction into the reactor, thereby cooling the recycle bottoms while gradually warming the energetic feed. The advantageous and novel results of this cooling/warming process is prevention of instability of the energetic feedstock, as well as the recycling of heat energy in the system, thereby reducing the size of the boiler package.

In another embodiment, the system for disposal of hydrazine propellants and other energetic materials is modular in design, whereby the entire system can be broken down into freightable modules for ease of shipping to source material locations, and reassembled as required.

In yet another embodiment, the second column operates at a higher pressure and lower temperature than the first column, preventing the undesired decomposition of organic material, thereby promoting stability of the system and minimizing coking.

A still further embodiment of the system involves the novel use of a two-stage reactor, whereby the energetic material is hydrotreated in a stacked two-stage reactor bed which enables the redistribution of the fluid phases and cost efficient fluid contact without additional piping and space requirements. In addition, the stacked, two stage reactor bed design facilitates transport by permitting shipment of the reactor skids to occur without exceeding predetermined shipping restrictions. The predetermined shipping restrictions are dictated by the size of conventional freight containers used aboard ships and tractor trailers. For example, freight containers having nominal lengths of 40 feet would restrict the size of a reactor section to be not greater than 40 feet, such that the reactor can to be broken down to freightable modules for shipment.

Another embodiment incorporates a process monitoring system, whereby the chemical components traveling through the process can be sampled and tested, advantageously ensuring optimum operation of the system. A gas chromatograph and related computer equipment is utilized for the chemical analysis and subsequent determination of the adequacy of the process.

Still other objects and advantages of the present invention will become readily apparent to those skilled in the art from the following detailed description, where I have shown and described only the preferred embodiment of the invention, simply by way of illustration of the best mode contemplated by me of carrying out my invention. As will be realized, the invention is capable of other and different embodiments, and its several details are capable of modifications in various obvious respects, all without departing from the invention. Accordingly, the drawings and descriptions are to be regarded as illustrative in nature, and not as restrictive.

BRIEF DESCRIPTION OF THE DRAWINGS

The invention will be more fully understood and further advantages will become apparent when reference is had to the following detailed description and the accompanying drawing, in which.

DESCRIPTION OF THE PREFERRED EMBODIMENTS

The present invention is directed to a unique apparatus configuration and novel method for the neutralization of hydrazine compounds. Hydrazine, derivatives of hydrazine, or other suitable energetic compounds, may be processed by the system resulting in new compounds having commercial value. Some of the product compounds from the process may be recycled into the system in a closed-loop configuration, resulting in reduced operating cost by reducing or eliminating the need for additional reactive materials.

Figure 1A:
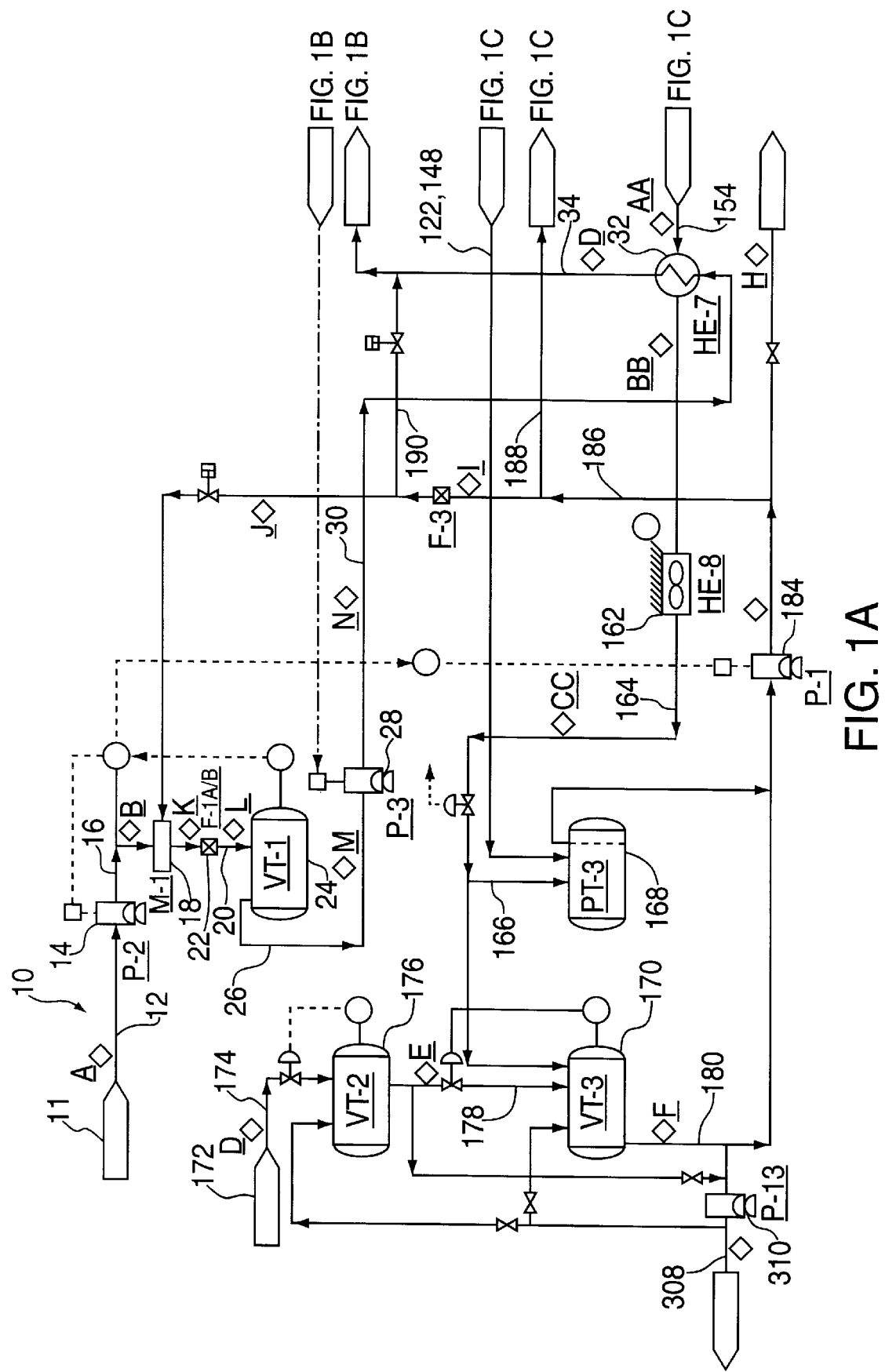
FIG. 1a is a partial schematic representation of a system configuration depicting the introduction of the feedstock into the system, and is linked with both FIGS. 1b and 1c.
Figure 1B:
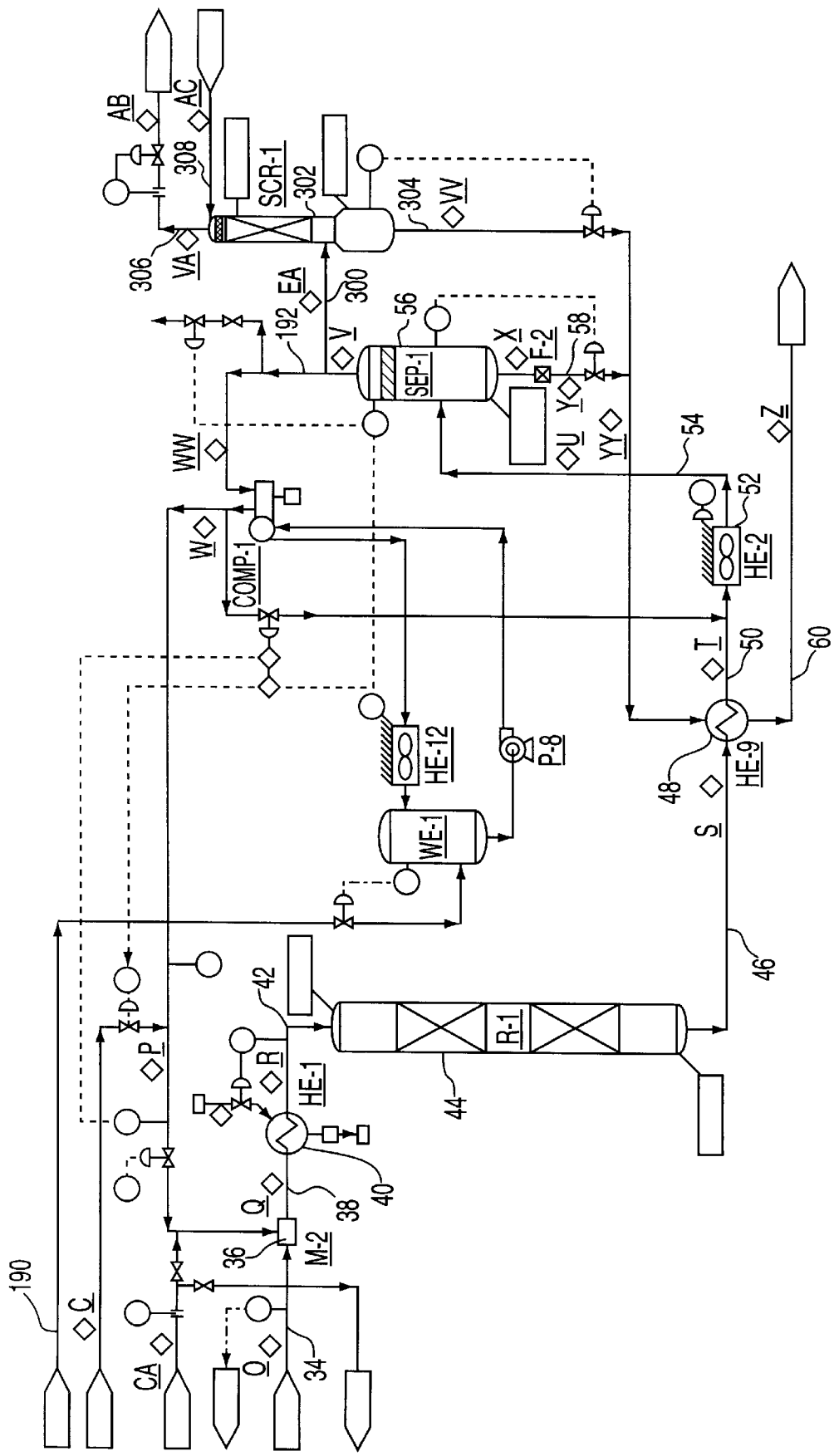
FIG. 1b is a partial schematic representation of a system configuration, linked with both FIGS. 1a and 1c, depicting the diluted feedstock as it is fed into the reactor portion of the system.
Figure 1C:
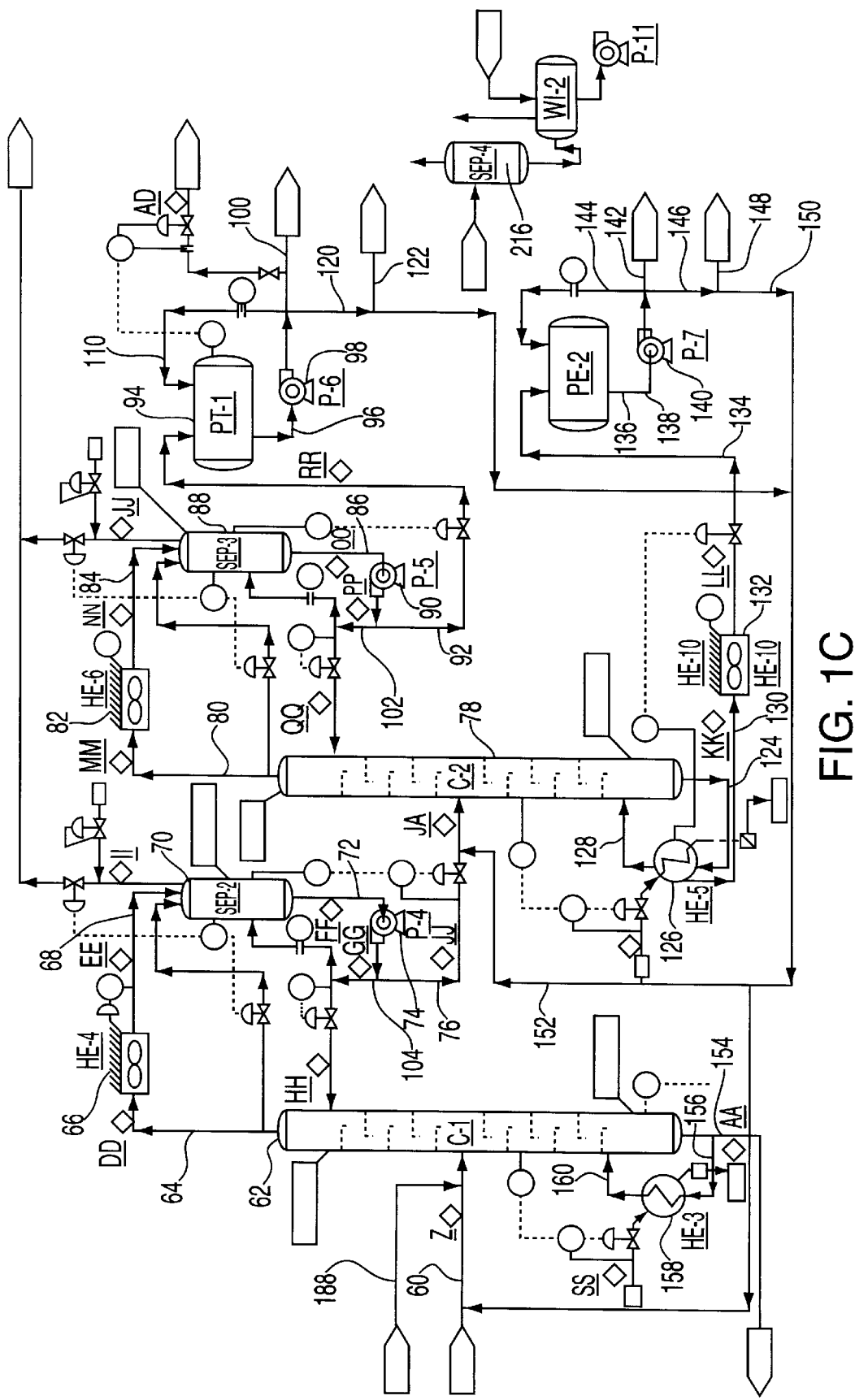
FIG. 1c is a partial schematic representation of a system configuration of the system depicting the distillation columns and the storage tanks for the final product, and is linked with both FIGS. 1a and 1b.
Figure 2:
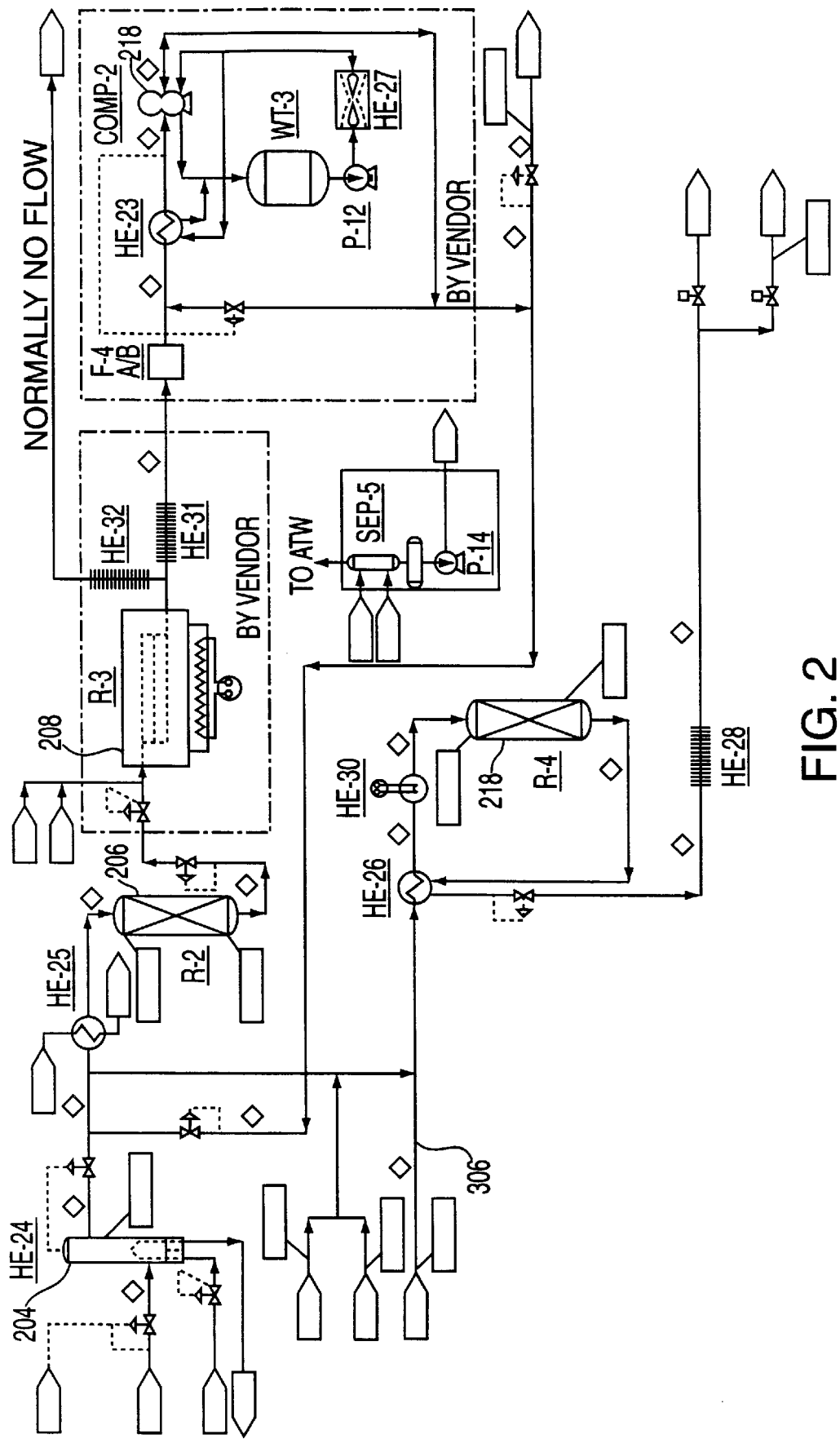
FIG. 2 is a partial schematic representation of a preferred embodiment of the invention of FIGS. 1a, 1b and 1c, the system providing for the neutralization of unsymmetrical dimethyl hydrazine, incorporating an ammonia dissociator and boiler package depicted in a closed-loop arrangement.

Referring now to the embodiment depicted in FIGS. 1a, 1b and 1c, these figures depicting a schematic representation of the entire system 10, and FIGS. 2 and 3, unsymmetrical dimethyl hydrazine (UDMH) is introduced into the system from a source 11 by the action of feed pump 14 on the feed line 12.

Tables 1a–1e, below, show the material balance for the preferred stream conditions depicted in FIGS. 1a–1c. For example, the stream conditions for the introduction of UDMH from the source 11 is such that the source material

TABLE 1A

| | MW | A 1 UDMH to P-2 | B 2 UDMH to M-1 | D 4 Makeup H2O to VT-2 | E 5 Makeup H2O to VT-3 | F 6 Recycle H2O to P-1 | G 7 Recycle Exit P-1 | H 8 Waste H20 | I 9 Recycle H20 to Filter | J 10 Recycle H20 to VT-1 |
|---|---|---|---|---|---|---|---|---|---|---|
| Phase => | | Liquid | Liquid | Liquid | Liquid | Liquid | Liquid | Liquid | Liquid | Liquid |
| Temperature, C. | | 20.0 | 20.0 | 20.0 | 20.0 | 45.0 | 45.0 | 45.0 | 45.0 | 45.0 |
| Pressure, PSIG | | 0.0 | 40.0 | 50.0 | 40.0 | 30.0 | 50.0 | 50.0 | 50.0 | 45.0 |
| Vapor Frac | | 0.000 | 0.000 | 0.000 | 0.000 | 0.000 | 0.000 | 0.000 | 0.000 | 0.000 |
| Molecular weight | | 60.0 | 60.0 | 18.0 | 18.0 | 18.0 | 18.0 | 18.0 | 18.0 | 18.0 |
| Density gm/cc | | 0.842 | 0.842 | 0.99 | 0.99 | 0.97 | 0.97 | 0.97 | 0.97 | 0.97 |
| Mole Flow, KMOL/HR | | 6.306 | 6.306 | 0.555 | 0.555 | 84.305 | 83.804 | 0.501 | 83.303 | 83.303 |
| Moss Flow, KC/HR | | 379.000 | 379.000 | 10.000 | 10.000 | 1518.776 | 1509.743 | 9.033 | 1500.710 | 1500.710 |
| Volume Flow, L/MN | | 7.7 | 7.7 | 0.2 | 0.2 | 25.991 | 25.836 | 0.2 | 25.7 | 25.7 |
| Entholpy, MMBTU/HR | | −0.303 | −0.303 | −0.150 | −0.150 | −22.712 | −22.577 | −0.135 | −22.442 | −22.442 |
| WATER, KG/HR | 18 | 0.000 | 0.000 | 10.000 | 10.000 | 1518.523 | 1509.491 | 9.032 | 1500.459 | 1500.459 |
| HYDROGEN, KG/HR | 2 | 0.000 | 0.000 | 0.000 | 0.000 | 0.000 | 0.000 | 0.000 | 0.000 | 0.000 |
| NITROGEN, KG/HR | 28 | 0.000 | 0.000 | 0.000 | 0.000 | 0.000 | 0.000 | 0.000 | 0.000 | 0.000 |
| AMMONIA KG/HR | 17 | 0.000 | 0.000 | 0.000 | 0.000 | 0.247 | 0.246 | 0.001 | 0.245 | 0.245 |
| DMA, KG/HR | 45 | 0.000 | 0.000 | 0.000 | 0.000 | 0.001 | 0.001 | 0.000 | 0.001 | 0.001 |
| TMA, KG/HR | 59 | 0.000 | 0.000 | 0.000 | 0.000 | 0.002 | 0.002 | 0.000 | 0.002 | 0.002 |
| MMA, KG/HR | 31 | 0.000 | 0.000 | 0.000 | 0.000 | 0.003 | 0.003 | 0.000 | 0.003 | 0.003 |
| CH4, KG/HR | 17 | 0.000 | 0.000 | 0.000 | 0.000 | 0.000 | 0.000 | 0.000 | 0.000 | 0.000 |
| UDMH, KH/HR | 60 | 379.000 | 379.000 | 0.000 | 0.000 | 0.000 | 0.000 | 0.000 | 0.000 | 0.000 |

| | K 11 Dilute UDMH to Filter | L 12 Dilute UDMH to VT-1 | M 13 Dilute UDMH to P-3 | N 14 Dilute UDMH to HE-7 | O 15 Dilute UDMH to M-2 | AA 27 Recycle H20 from C-1 | BB 28 Recycle H20 Exiting HE-7 | CC 29 Recycle H20 to VT-3 | AC 83 Recycle H20 to Scrubber |
|---|---|---|---|---|---|---|---|---|---|
| Phase => | Liquid | Liquid | Liquid | Liquid | Liquid | Liquid | Liquid | Liquid | Liquid |
| Temperature, C. | 73.0 | 73.0 | 73.0 | 73.7 | 114.0 | 179.6 | 146.2 | 45.0 | 45.0 |
| Pressure, PSIG | 40.0 | 35.0 | 30.0 | 500.0 | 495.0 | 129.0 | 123.0 | 110.0 | 350 |
| Vapor Frac | 0.000 | 0.000 | 0.000 | 0.000 | 0.000 | 0.000 | 0.000 | 0.000 | 0.000 |
| Molecular weight | 20.96 | 20.96 | 20.96 | 20.96 | 20.96 | 18.0 | 18.0 | 18.0 | 18.0 |
| Density gm/cc | 0.94 | 0.94 | 0.94 | 0.94 | 0.88 | 0.83 | 0.90 | 0.972 | 0.97 |
| Mole Flow, KMOL/HR | 89.609 | 90.164 | 90.719 | 90.164 | 90.164 | 100.457 | 100.457 | 100.457 | 16.7 |
| Moss Flow, KC/HR | 1879.710 | 1889.710 | 1899.710 | 1889.710 | 1889.710 | 1809.743 | 1809.743 | 1809.743 | 300.00 |
| Volume Flow, L/MN | 33.364 | 33.531 | 33.696 | 34.1 | 35.9 | 36.4 | 34.8 | 31.0 | 5.1 |
| Entholpy, MMBTU/HR | −22.745 | −22.895 | −23.045 | −22.896 | −22.592 | −25.983 | −26.287 | −26.063 | −4.486 |
| WATER, KG/HR | 1500.459 | 1510.459 | 1510.459 | 4510.459 | 1510.459 | 1809.441 | 1809.441 | 1809.441 | 299.950 |
| HYDROGEN, KG/HR | 0.000 | 0.000 | 0.000 | 0.000 | 0.000 | 0.000 | 0.000 | 0.000 | 0.000 |
| NITROGEN, KG/HR | 0.000 | 0.000 | 0.000 | 0.000 | 0.000 | 0.000 | 0.000 | 0.000 | 0.000 |
| AMMONIA KG/HR | 0.245 | 0.245 | 0.245 | 0.245 | 0.245 | 0.296 | 0.296 | 0.296 | 0.049 |
| DMA, KG/HR | 0.001 | 0.001 | 0.001 | 0.001 | 0.001 | 0.002 | 0.002 | 0.002 | 0.000 |
| TMA, KG/HR | 0.002 | 0.002 | 0.002 | 0.002 | 0.002 | 0.002 | 0.002 | 0.002 | 0.000 |
| MMA, KG/HR | 0.003 | 0.003 | 0.003 | 0.003 | 0.003 | 0.004 | 0.004 | 0.004 | 0.001 |
| CH4, KG/HR | 0.000 | 0.000 | 0.000 | 0.000 | 0.000 | 0.000 | 0.000 | 0.000 | 0.000 |
| UDMH, KH/HR | 379.000 | 379.00 | 379.00 | 379.00 | 379.00 | 0.000 | 0.000 | 0.000 | 0.000 | is liquid UDMH, flowing at up to 379 Kg/Hr as a result of the action of pumps 14 on feed line 12, at an ambient temperature of approximately 20° C.

TABLE 1B

START OF RUN (SOR)

| | MW | CA 3H MAKEUP 120 | EA 5H OFF GAS PURGE | O 15 DILUTE UDMH TO M-2 | P 16 RECYCLE H2 | Q 17 R-1 FEED COLD | R 18 R-1 FEED HOT | S 19 R-1 EXIT HOT | T 20 R-1 EXIT COLD |
|---|---|---|---|---|---|---|---|---|---|
| Phase | | VAPOR | VAPOR | LIQUID | VAPOR | MIXED | MIXED | MIXED | MIXED |
| Temperature, C. | | 160.0 | 60.0 | 114.0 | 110.1 | 107.0 | 150.0 | 166.0 | 144.0 |
| Pressure, PSIG | | 420.0 | 340.0 | 420.0 | 495.0 | 415.0 | 375.0 | 350.0 | 346.0 |
| Vapor Froc | | 1.000 | 1.000 | 0.000 | 1.000 | 0.362 | 0.417 | 0.493 | 0.404 |
| Molecular weight | | 8.82 | | 20.96 | 15.8 | 18.5 | 18.5 | 18.5 | 18.5 |
| Density gm/cc | | 0.0088 | | 0.88 | 0.016 | — | — | — | — |
| Mole Flow, KMOL/HR | | 12.7 | 6.2 | 90.2 | 38.0 | 140.9 | 140.9 | 140.9 | 140.9 |
| Mass Flow, KG/HR | | 112.01 | 98.33 | 1889.71 | 601.02 | 2602.74 | 2602.74 | 2602.74 | 2602.74 |
| Volume Flow, L/MIN | | 254.5 | 117.3 | 35.9 | 574.1 | 978.4 | 1317.7 | 1708.0 | 1359.6 |
| Entholpy, MMBTU/HR | | 0.028 | −0.014 | −22.592 | −0.031 | −22.594 | −21.917 | −21.385 | −21.977 |
| WATER, KG/HR | 18 | 0.000 | 0.813 | 1510.459 | 4.958 | 1515.427 | 1515.427 | 1515.427 | 1515.427 |
| HYDROGEN, KG/HR | 2 | 18579 | 5.800 | 0.000 | 35.455 | 54.033 | 54.033 | 41.320 | 41.320 |
| NITROGEN, KG/HR | 28 | 85931 | 86.426 | 0.000 | 528.270 | 615.201 | 615.201 | 615.201 | 615.201 |
| AMMONIA, KG/HR | 17 | 4.989 | 0.960 | 0.245 | 5.866 | 11.100 | 11.100 | 118.125 | 118.125 |
| DMA, KG/HR | 45 | 0.000 | 2.899 | 0.001 | 17.719 | 17.720 | 17.720 | 296.647 | 296.647 |

TABLE 1-C

| | MW | MAKEUP H20 | OFF GAS PURGE | O 15 DILUTE UDMH TO M-2 | P 16 RECYCLE H2 | Q 17 R-1 FEED COLD | R 18 R-1 FEED HOT | S 19 R-1 EXIT HOT | T 20 R-1 EXIT COLD |
|---|---|---|---|---|---|---|---|---|---|
| Phase | | Vapor | Vapor | Liquid | Vapor | Mixed | Mixed | Mixed | Mixed |
| Temp. C. | | 160.0 | 60.0 | 114.0 | 110.1 | 109.0 | 170.0 | 186.0 | 144.0 |
| Pressure, PSIG | | 495.0 | 340.0 | 495.0 | 495.0 | 490.0 | 450.0 | 350.0 | 345.0 |
| Vapor Frac | | 1.000 | 1.000 | 0.000 | 1.000 | 0.359 | 0.452 | 0.675 | 0.404 |
| Molecular wgt | | 8.82 | 15.82 | 20.96 | 15.82 | 18.5 | 18.5 | 18.5 | 18.5 |
| Density gm/cc | | 0.009 | 0.016 | 0.88 | 0.016 | — | — | — | — |
| Mole flow, KMOL/HR | | 12.7 | 6.2 | 90.2 | 38.0 | 140.9 | 140.9 | 140.9 | 140.9 |
| Mass flow, KG/HR | | 112.01 | 98.33 | 1889.71 | 601.03 | 2602.76 | 2602.76 | 2602.76 | 2602.76 |
| Volume flow, L/MIN | | 217.0 | 117.3 | 35.9 | 574.1 | 829.9 | 1255.2 | 2423.7 | 1359.6 |
| Enthalpy, MMBTU/HR | | 0.028 | −0.014 | −22.592 | −0.031 | −22.594 | −21.545 | −20.442 | −21.977 |
| Water, KG/HR | 18 | 0.000 | 0.813 | 1510.459 | 4.968 | 1515.427 | 1515.427 | 1515.427 | 1515.427 |
| Hydrogen, KG/HR | 2 | 18.579 | 5.800 | 0.000 | 35.455 | 54.033 | 54.033 | 41.321 | 41.321 |
| Nitrogen, KG/HR | 28 | 86.931 | 86.427 | 0.000 | 528.273 | 615.204 | 615.204 | 615.204 | 615.204 |
| Ammonia, KG/HR | 17 | 4.989 | 0.960 | 0.245 | 5.866 | 11.101 | 11.101 | 118.125 | 118.125 |
| DMA, KG/HR | 45 | 0.000 | 2.899 | 0.001 | 17.719 | 17.720 | 17.720 | 296.647 | 296.647 |
| TMA, KG/HR | 59 | 0.000 | 0.025 | 0.002 | 0.151 | 0.152 | 0.152 | 3.033 | 3.033 |
| MNA, KG/HR | 31 | 0.025 | 0.013 | 0.003 | 0.077 | 0.106 | 0.106 | 2.986 | 2.986 |
| CH4, KG/HR | 16 | 1.487 | 1.395 | 0.000 | 8.524 | 10.011 | 10.011 | 10.011 | 10.011 |
| UDMH, KG/HR | 60 | 0.000 | 0.000 | 379.000 | 0.000 | 379.000 | 379.000 | 0.000 | 0.000 |

| U 21 SEP-1 FEED | V 22 SEP-1 VAPORS | W 22a SCRUBBER UNDERFLOW | VA 22C SCRUB. EXIT VAPORS | WW 23A COMP-1 FEED | X 24 SEP-1 UNDERFLOW | YY 25A C-1 FEED COLD | Z 26 C-1 FEED HOT | AB 48 OFF-GASS to BOILER | AC 83 RECYCLE H20 SCRUBBER |
|---|---|---|---|---|---|---|---|---|---|
| Mixed | Vapor | Liquid | Vapor | Vapor | Liquid | Liquid | Mixed | Vapor | Liquid |
| 60.0 | 60.0 | 51.1 | 45.2 | 60.0 | 60.0 | 59.2 | 165.7 | 45.0 | 45.0 |
| 340.0 | 340.0 | 340.0 | 340.0 | 340.0 | 340.0 | 150.0 | 132.0 | 70.0 | 350.0 |
| 0.306 | 1.000 | 0.000 | 1.000 | 1.000 | 0.000 | 0.000 | 0.088 | 1.000 | 0.000 |
| 18.5 | 15.8 | 18.1 | 15.5 | 15.5 | 19.7 | 19.6 | 19.6 | 15.5 | 18.0 |
| — | 0.016 | 0.96 | 0.016 | 0.016 | 0.886 | 0.895 | — | — | 0.973 |
| 140.9 | 44.2 | 16.8 | 6.1 | 38.0 | 96.7 | 113.5 | 113.5 | 6.1 | 16.7 |
| 2602.77 | 699.36 | 304.34 | 93.99 | 601.03 | 1903.40 | 2207.74 | 2207.74 | 93.99 | 300.00 |
| 851.5 | 834.6 | 5.3 | 109.5 | 717.2 | 36.2 | 41.4 | 642.2 | 437.9 | 5.1 |
| −23.301 | −0.099 | −4.492 | −0.008 | −0.085 | −23.199 | −27.691 | −26.157 | −0.007 | −4.486 |
| 1515.427 | 5.781 | 300.329 | 0.434 | 4.968 | 1509.646 | 1809.975 | 1809.975 | 0.434 | 299.950 |
| 41.322 | 41.255 | 0.005 | 5.795 | 35.455 | 0.067 | 0.073 | 0.073 | 5.795 | 0.000 |
| 615.213 | 614.700 | 0.056 | 86.371 | 528.273 | 0.513 | 0.569 | 0.569 | 86.371 | 0.000 |
| 118.125 | 6.826 | 1.007 | 0.002 | 5.866 | 111.299 | 112.307 | 112.307 | 0.002 | 0.049 |
| 296.647 | 20.618 | 2.898 | 0.001 | 17.719 | 276.029 | 278.927 | 278.927 | 0.001 | 0.000 |
| 3.033 | 0.176 | 0.025 | 0.000 | 0.151 | 2.858 | 2.883 | 2.883 | 0.000 | 0.000 |

TABLE 1-C-continued

| 2.987 | 0.090 | 0.013 | 0.000 | 0.077 | 2.897 | 2.910 | 2.910 | 0.000 | 0.001 |
|---|---|---|---|---|---|---|---|---|---|
| 10.012 | 9.918 | 0.007 | 1.387 | 8.524 | 0.093 | 0.101 | 0.101 | 1.387 | 0.000 |
| 0.000 | 0.000 | 0.000 | 0.000 | 0.000 | 0.000 | 0.000 | 0.000 | 0.000 | 0.000 |

TABLE 1D

| | | Stream No. => | | | | | |
|---|---|---|---|---|---|---|---|
| | M.W. | Z 26<br>C-1 Feed | AA 27<br>C-1 Bottom | DD 30<br>C-1<br>Overhead<br>Hot | EE 31<br>C-1<br>Overhead<br>Cold | HH 34<br>C-1 Reflux | II 35<br>C-1 Vent |
| Phase => | | LIQUID | LIQUID | VAPOR | LIQUID | LIQUID | VAPOR |
| Temperature, C. | | 111.0 | 179.6 | 82.2 | 40.0 | 40.0 | 40.0 |
| Pressure, PSIG | | 132.0 | 129.0 | 126.0 | 122.0 | 122.0 | 122.0 |
| Vapor Froc | | 0.000 | 0.000 | 1.000 | 0.001 | 0.000 | 1.000 |
| Molecular weight | | 19.5 | 18.0 | 30.7 | 30.7 | 30.7 | 16.37 |
| Density gm/cc | | 0.837 | 0.829 | 0.012 | 0.645 | 0.645 | 0.012 |
| Mole Flow, KMOL/HR | | 113.455 | 100.457 | 86.242 | 86.242 | 73.240 | 0.104 |
| Moss Flow, KG/HR | | 2207.74 | 1809.74 | 2648.28 | 2648.28 | 2250.28 | 1.70 |
| Volume Flow, L/MIN | | 44.4 | 36.4 | 4377.3 | 4377.3 | 59.1 | 4.7 |
| Entholpy, MMBTU/HR | | −27.100 | −25.983 | −2.441 | −6.05 | −3.970 | −0.003 |
| WATER, KG/HR | 18 | 1809.975 | 1809.441 | 4.666 | 4.666 | 3.967 | 0.000 |
| HYDROGEN, KG/HR | 2 | 0.073 | 0.000 | 0.141 | 0.141 | 0.068 | 0.061 |
| NITROGEN, KG/HR | 28 | 0.569 | 0.000 | 2.274 | 2.274 | 1.706 | 0.268 |
| AMMONIA, KC/HR | 17 | 112.306 | 0.296 | 742.675 | 742.675 | 630.710 | 0.891 |
| DMA, KG/HR | 45 | 278.927 | 0.002 | 1859.519 | 1859.519 | 1580.705 | 0.435 |
| TMA, KG/HR | 59 | 2.883 | 0.002 | 19.193 | 19.193 | 16.316 | 0.004 |
| MMA, KG/HR | 31 | 2.910 | 0.004 | 19.307 | 19.307 | 16.404 | 0.015 |
| CH4, KG/HR | 17 | 0.101 | 0.000 | 0.507 | 0.507 | 0.407 | 0.029 |
| UDWH, KG/HR | 60 | 0.000 | 0.000 | 0.000 | 0.000 | 0.000 | 0.000 |

| | Stream No. => | | | | | | |
|---|---|---|---|---|---|---|---|
| | JA 36A<br>C-2 Feed | KK 37<br>DMA<br>PROD. TO<br>PT-2 | MM 39<br>C-2<br>Overhead<br>Hot | NN 40<br>C-2<br>Overhead<br>Cold | QQ 43<br>C-2<br>Reflux | RR 44<br>MH3<br>PROD. TO<br>TO PT-1 | SS 45<br>C-2<br>Vent | AD 60<br>NH3 PROD.<br>H2<br>GENERATION |
| Phase => | LIQUID | LIQUID | VAPOR | LIQUID | LIQUID | LIQUID | VAPOR | LIQUID |
| Temperature, C. | 40.0 | 107.0 | 47.0 | 41.1 | 41.1 | 41.1 | 41.1 | 41.1 |
| Pressure, PSIG | 250.0 | 252.0 | 250.0 | 240.0 | 254.7 | 250.0 | 240.0 | 240.0 |
| Vapor Froc | 0.000 | 0.000 | 1.000 | 0.000 | 0.000 | 0.000 | 1.000 | 0.000 |
| Molecular weight | 30.7 | 45.0 | 17.2 | 17.2 | 17.2 | 17.2 | 17.4 | 17.2 |
| Density gm/cc | 0.645 | 0.54 | 0.017 | | 0.568 | 0.568 | 0.017 | 0.568 |
| Mole Flow, KMOL/HR | 12.894 | 6.258 | 41.6 | 41.6 | 35.0 | 6.504 | 0.133 | 6.504 |
| Moss Flow, KG/HR | 396.30 | 282.0 | 717.1 | 717.1 | 602.6 | 112.0 | 2.31 | 112.0 |
| Volume Flow, L/MIN | 10.4 | 8.9 | 1013.3 | 26.00 | 17.4 | 3.2 | 3.3 | 3.2 |
| Entholpy, MMBTU/HR | −0.697 | −0.184 | −1.766 | −2.57 | −2.11 | −0.393 | −0.005 | −0.393 |
| WATER, KG/HR | 0.534 | 0.68 | 0.000 | 0.000 | 0.000 | 0.000 | 0.000 | 0.000 |
| HYDROGEN, KG/HR | 0.012 | 0.000 | 0.04 | 0.04 | 0.03 | 0.005 | 0.007 | 0.005 |
| NITROGEN, KG/HR | 0.301 | 0.000 | 0.625 | 0.625 | 0.330 | 0.061 | 0.240 | 0.061 |
| AMMONIA, KC/HR | 111.120 | 0.001 | 698.2 | 698.2 | 587.1 | 109.094 | 2.026 | 109.094 |
| DMA, KG/HR | 278.491 | 276.37 | 0.091 | 0.091 | 0.076 | 0.014 | 0.000 | 0.014 |
| TMA, KG/HR | 2.877 | 2.86 | 0.0005 | 0.0005 | 0.0005 | 0.000 | 0.000 | 0.000 |
| MMA, KG/HR | 2.892 | 0.072 | 17.8 | 17.8 | 14.99 | 2.790 | 0.013 | 2.790 |
| CH4, KG/HR | 0.072 | 0.000 | 0.348 | 0.348 | 0.277 | 0.052 | 0.02 | 0.052 |
| UDWH, KG/HR | 0.000 | 0.000 | 0.000 | 0.000 | 0.000 | 0.000 | 0.000 | 0.000 |

TABLE 1E

END OF RUN (EOR)

| | M.W. | 3H<br>H2 From<br>Comp-2 Δ | 5H<br>Off Gas<br>Purge | 15<br>Dilute<br>UDMH<br>to M-2 | 16<br>Recycle<br>H2 | 17<br>B-1 Feed<br>Cold | 18<br>B-1 Feed<br>Cold Δ | 19<br>P-1 Exit<br>Hot Δ | 20<br>B-1 Exit<br>Hot Δ | 21<br>SEP-1<br>Feed |
|---|---|---|---|---|---|---|---|---|---|---|
| Phase | | VAPOR | VAPOR | LIQUID | VAPOR | MIXED | MIXED | MIXED | MIXED | MIXED |
| Temperature, C. | | 160.0 | 60.0 | 115.0 | 109.3 | 108.7 | 170.0 | 196.0 | 165.8 | 60.0 |
| Pressure, PSIG | | 495.0 | 340.0 | 495.0 | 495.0 | 455.0 | 450.0 | 350.0 | 345.0 | 340.0 |
| Vapor Frac | | 1.000 | 1.000 | 0.000 | 1.000 | 0.366 | 0.483 | 0.711 | 0.528 | 0.320 |
| Molecular weight | GAS | 8.82 | 15.87 | 20.89 | 15.87 | 14.36 | 18.22 | 18.366 | 17.0 | 18.71 |
| | LIQ | | | | | 20.78 | 20.00 | 18.695 | 18.96 | 18.72 |
| Density gm/cc | GAS | 0.009 | 0.014 | 0.873 | 0.018 | 0.15 | 0.14 | 0.12 | 0.012 | 0.14 |
| | LIQ | | | | | | 0.790 | 0.795 | 18.695 | |
| Mole Flow, KMOL/HR | | 12.670 | 8.867 | 92.363 | 40.81 | 145.843 | 145.843 | 145.843 | 145.843 | 145.843 |
| Mass Flow, KG/HR | | 111.817 | 106.046 | 1929.710 | 647.447 | 2696.974 | 2696.974 | 2688.974 | 2688.974 | 2688.974 |
| Volume Flow, L/MIN | | 216.4 | 126.0 | 36.8 | 615.4 | 909.1 | 1381.832 | 2641.352 | 1130.496 | 917.942 |
| Entholpy, MMBTU/HR | | 0.028 | −0.036 | −22.358 | −0.161 | −22.490 | −21.332 | −20.992 | −22.023 | −23.957 |
| WATER, KG/HR | 18 | 0.000 | 0.856 | 1550.162 | 5.234 | 1555.396 | 1555.396 | 155.396 | 155.396 | 155.396 |
| HYDROGEN, KG/HR | 2 | 18.508 | 5.752 | 0.000 | 35.157 | 53.666 | 53.666 | 40.957 | 40.957 | 40.957 |
| NITROGEN, KG/HR | 28 | 86.678 | 86.323 | 0.000 | 527.683 | 614.315 | 614.315 | 614.315 | 614.316 | 619.662 |
| AMMONIA KG/HR | 17 | 4.981 | 9.422 | 0.000 | 57.589 | 62.570 | 52.570 | 169.662 | 169.662 | 169.662 |
| DMA, KG/HR | 45 | 0.007 | 1.997 | 0.539 | 12.208 | 12.754 | 12.754 | 293.091 | 293.091 | 293.091 |
| TMA, KG/HR | 59 | 0.000 | 0.083 | 0.003 | 0.129 | 132 | 132 | 2.267 | 2.267 | 2.267 |
| MMA, KG/HR | 31 | 0.019 | 0.073 | 0.006 | 0.078 | 0.103 | 0.103 | 2.236 | 2.236 | 2.236 |
| CH4, KG/HR | 16 | 1.625 | 1.540 | 0.000 | 9.413 | 11.038 | 11.038 | 11.038 | 11.038 | 11.038 |
| UDMH, KH/HR | 60 | 0.000 | 0.000 | 379.000 | 0.000 | 379.000 | 379.000 | 0.000 | 0.000 | 0.000 |

| | 22<br>Sep-1<br>Vapors Δ | 22A<br>Scrubber<br>Under<br>flow | 22C<br>Scrub Exit<br>Vapors | 23A<br>Comp-1<br>Feed | 24<br>Sep-1<br>Under<br>flow | 25A<br>0-1 Geed<br>Cold | 26<br>0-1 Feed<br>Hot Δ | 48<br>Off-Gas<br>to<br>Boiler | 83<br>Recycle<br>H20<br>to Scrubber |
|---|---|---|---|---|---|---|---|---|---|
| Phase | VAPOR | LIQUID | LIQUID | VAPOR | LIQUID | LIQUID | MIXED | VAPOR | LIQUID |
| Temperature, C. | 60.0 | 63.6 | 47.7 | 60.0 | 60.0 | 59.8 | 145.0 | 45.0 | 45.8 |
| Pressure, PSIG | 340.0 | 340.0 | 340.0 | 340.0 | 340.0 | 140.0 | 132.0 | 70.0 | 360.0 |
| Vapor Frac. | 1.000 | 0.000 | 1.000 | 1.000 | 0.000 | 0.000 | 0.06 | 1.000 | 0.000 |
| Molecular weight | 15.865 | 18.056 | 15.538 | 15.865 | 19.7 | 19.4 | 20.0<br>19.3 | 15.538 | 18.02 |
| Density gm/cc | 0.014 | 0.937 | 0.014 | 0.014 | 0.0880 | 0.0889 | 0.000<br>0.000 | 0.003 | 0.972 |
| Mole Flow, KMOL/HR | 47.496 | 17.273 | 6.052 | 40.810 | 98.357 | 115.630 | 115.630 | 6.052 | 16.649 |
| Mass Flow, KC/HR | 753.482 | 311.964 | 94.159 | 847.447 | 1935.471 | 2247.365 | 2247.365 | 94.159 | 300.00 |
| Volume Flow, L/MN | 896.401 | 5.545 | 110.014 | 770.367 | 36.643 | 42.1 | 2710.6 | 456.900 | 5.143 |
| Entholpy, MMBTU/HR | −0.255 | −4.510 | −0.009 | 0.219 | 23.700 | 28.210 | 27.18 | 0.01 | −4.483 |
| WATER, KG/HR | 0.090 | 300.257 | 0.489 | 5.234 | 1549.306 | 1849.583 | 1849.583 | 0.489 | 299.991 |
| HYDROGEN, KG/HR | 40.909 | 0.007 | 5.745 | 35.157 | 0.048 | 0.055 | 0.055 | 5.745 | 0.000 |
| NITROGEN, KG/HR | 613.961 | 0.058 | 86.264 | 527.638 | 0.355 | 0.413 | 0.413 | 96.264 | 0.000 |
| AMMONIA KG/HR | 67.011 | 9.421 | 0.001 | 57.589 | 102.651 | 112.071 | 112.071 | 0.001 | 0.000 |
| DMA, KG/HR | 14.205 | 2.0950 | 0.010 | 12.208 | 278.996 | 280.961 | 280.961 | 0.010 | 0.108 |
| TMA, KG/HR | 0.212 | 0.022 | 0.061 | 0.129 | 2.055 | 2.077 | 2.077 | 0.061 | 0.001 |
| MMA, KG/HR | 0.151 | 0.014 | 0.069 | 0.078 | 2.095 | 2.099 | 2.099 | 0.059 | 0.001 |
| CH4, KG/HR | 10.963 | 0.010 | 1.530 | 9.413 | 0.085 | 0.095 | 0.095 | 1.530 | 0.000 |
| UDMH, KH/HR | 0.000 | 0.000 | 0.000 | 0.000 | 0.000 | 0.000 | 0.000 | 0.000 | 0.000 |

Feed pump output line 16, connected to the pump 14, introduces the UDMH into a first mixing T 18, where the feed UDMH is diluted with a liquid, preferably water, moderating the effect of the exothermic heat of reaction that occurs during hydrotreating resulting in a cooler, and safer, system. The diluting liquid is mostly water from various sources, both fresh water and recycled water, and is introduced via line 186 into the mixing T 18.

The water make-up 172 is introduced into the system via line 174 and introduced into surge tank 176. Surge tank 176, containing generally pure water, is connected to surge tank 170 via line 178. Water exits surge tank 170 via surge tank output line 180, and is introduced to pump 184. Pump output line 186 is used to introduce water into the first mixing T 18 as described above.

The output of the first mixing T 18 comprises dilute energetic material which is transported through the mixing T output line 20 and is introduced into the first surge tank 24. Tank 24 is utilized to hold the dilute energetic material in order to prevent surges of pure or highly concentrated UDMH, or other suitable feedstock, from proceeding in the system. The diluted energetic material exits the holding tank 24 through output line 26, which directs the feedstock to pump 28, for pumping through pump output line 30 to a heat exchanger 32. The feedstock is advantageously warmed as it passes through the heat exchanger 32 into the heat exchanger output line 34. The heat source for heat exchanger 32 is preferably the warm intermediate or product from elsewhere in the system, advantageously recycling the heat energy and reducing the amount of externally produced and supplied heat into the system.

Heat exchanger output line 34 directs the feedstock to a second mixing T 36, depicted in FIG. 1b, where the feedstock is combined with hydrogen gas. Hydrogen gas for the catalytic reaction is introduced into mixing T 36 from hydrogen input line 108. The second mixing T output line 38 directs the mixed phase feedstock to a heat exchanger 40, where the temperature of the feedstock is increased as required for the hydrotreating reactions to proceed efficiently.

Heat exchanger output line 42 then directs the feedstock, which has been diluted with water and combined with hydrogen, into reactor 44. The reactor 44 is a co-current downflow dual bed hydrotreating reactor, which has been optimized for this feedstock. Once through the reactor 44, the feedstock exits the reactor through reactor output line 46 and is cooled as it passes through heat exchanger 48. Reactor output effluent proceeds in its primary path through the heat exchange output line 50 and proceeds into a thin fan cooler heat exchanger 52 for further cooling, continuing through output line 54 where the reactor output effluent is then introduced into a first separation tank 56. Separator tank 56 is a high pressure gas liquid separator wherein the reactor effluent is further cooled in order to efficiently separate the gaseous component from the liquid effluent. Hydrogen gas from the first separation tank 56 is removed through overhead flow line 192, and the hydrogen gas directed back to the second mixing T 36 for introduction into the diluted feedstock. This recycles unused hydrogen gas, reducing the need for additional externally supplied hydrogen for this system. Alternatively, the hydrogen gas withdrawn from separation tank 56 may be routed to the boiler package 194 and utilized as fuel, resulting in the complete use of recycled material and minimizing the need for externally supplied fuel for the boiler package.

Effluent from the first separation tank 56 proceeds through first separation tank output line 58, continuing on through heat exchanger 48 where the effluent is warmed, into heat exchanger output line 60, where the effluent is introduced into the first distillation column 62 for separation of the reactor products. Warming of the effluent in heat exchanger 48 results from the hot reactor effluent passing concurrently through the heat exchanger. In this manner the separator effluent is prewarmed prior to entry into the first distillation column 62, while resultant heat from the reactor is recycled.

Overhead from the first distillation column 62, preferably comprising product amines and ammonia, is withdrawn via distillation column overhead withdrawal line 64 and cooled through heat exchanger 66, the overhead proceeding through heat exchange output line 68 and into the second separation tank, or reflux drum 70. Effluent from the reflux drum 70, still comprising mostly amines and ammonia, may be withdrawn and routed through reflux drum output line 72 which feeds into pump 74, which then routes the effluent to either the first distillation column 62 or to the second distillation column 78. Routing of the first distillation column overhead in this manner places the first distillation column 62 under reflux for further separation, as is known to one skilled in the art. The result is that the first distillation column 62 is placed under reflux to a predetermined reflux ratio, thereby allowing a predetermined optimum volume of condensed liquid in the reflux drum 70 to be routed back to the first distillation column 62. Output effluent from pump 74 may continue through pump output line 76 feeding effluent into a second distillation column 78 for the separation of the amines from the ammonia products.

Overhead from the second distillation column 78, preferably comprising ammonia products, proceeds through the second distillation column overhead withdrawal line 80, is cooled through heat exchanger 82, and continues through heat exchanger output line 84 where the cooled overhead is introduced into a third separation tank, or reflux drum 86.

Effluent from the third reflux drum 86 enters the third reflux drum output line 88 where it is introduced into pump 90. Output from pump 90 may be introduced into pump output line 102, where the effluent is reintroduced into the second distillation column 78, placing the second distillation column 78 in reflux for further separation, as is known in the art. A portion of the output effluent, the ammonia product, is pumped by pump 90 into pump output line 92 and discharged into receiver tank 94.

The ammonia product collected in product tank 94 may be withdrawn through output line 96 into pump 98, with pump output line 100 carrying the product for further processing as may be desired. Additionally, pump 98 can be used for recirculation of the product in product tank 94 in order to keep the material uniform. Alternatively, pump output line 120 can return the ammonia product to either the second distillation column 78 by introducing the product into line 152, or the product can be reintroduced into line 60 and, continuing into the first distillation column 62 for reprocessing. Continued reprocessing of the ammonia product through the reintroduction of the product into either the first distillation column 62 or the second distillation column 78 ensures complete processing of the energetic feed material. However, the material processed through the distillation columns is generally performed as part of a continuous operation, and the material being processed is not generally returned for further processing once an optimum reflux ratio and other related conditions are established, resulting in the highest quality of output material on a continuous processing basis.

Bottoms from the second distillation column 78, containing mostly amine products, may be withdrawn through bottoms output line 124 where the bottoms are routed through heat exchanger 126 and cooled. Output of heat exchanger 126 is routed through heat exchange output line 128, and the heated bottoms reintroduced into the second distillation column 78 for further separation of the amine products from the ammonia products.

Alternatively, output bottoms from distillation column 78 may exit heat exchanger 126 through heat exchanger output line 130 and cools as it passes through heat exchanger 132. The cooled second distillation column bottoms proceed through heat exchange line 134 and are introduced into product tank 136. This product, mostly dimethyl amine (DMA), may be withdrawn from product tank 136 through product tank output line 138 and introduced into pump 140. Pump output line 142 directs the DMA for product loading. Additionally, pump 140 can be used for recirculation of the product in product tank 136 in order to keep the material uniform.

Alternate pump output line 144 returns the DMA to the product tank 136. Additionally, alternate pump output line 146 is used to direct any off spec DMA to either the third receiver tank 168 or alternatively, through line 150 returning the DMA product either to the input of the second distillation column 78 via line 152, or to the first distillation column 62 via line 60 for reprocessing.

In another unique embodiment of the present invention, warm bottoms from first distillation column 62, containing mostly water, are used to warm the diluted feedstock prior to introduction into the reactor 44, advantageously recycling the heat energy and reducing the amount of externally produced and supplied heat into the system. Bottoms from the first distillation column 62 are withdrawn through the first distillation column bottoms output line 154, the first distillation column bottoms being routed to heat exchanger 32 where the bottoms are cooled as the feedstock is warmed. Following passage of the first distillation column bottoms through heat exchanger 32, the bottoms are further cooled flowing through heat exchanger 162, heat exchange output line 164 continuing the flow of the first distillation column bottoms into either product tank 168 or a surge tank 170. Surge tank 170, containing mostly recycled water from the first distillation column bottoms, is used to isolate the flow to the reactor 44 from the flow from the first distillation column bottoms.

In another embodiment, off-spec water exiting pump 184 via pump output line 188, is directed to the first distillation column 62 for further separation of the various products from the water. Alternately, flow of the recycled water through pump 184 is to line 190 for mixture with the feed stock at mixing T 36, where any off-spec material is combined with the feed material for processing through the reactor 44.

In another advantageous embodiment of the present invention, pump 74 increases the pressure of the effluent from reflux drum 70. This results in the second distillation column 78 operating at a pressure higher than the operating pressure of the first distillation column 62. In this manner, undesired decomposition of organic material in column 162 is advantageously avoided, thereby promoting stability of the system and minimizing formation of undesired products.

In a highly preferred embodiment which will now be described, ammonia collected in the second receiver tank 94, is routed to an ammonia dissociator system 200, where the ammonia is dissociated into hydrogen and nitrogen.

Referring to FIG. 2, an ammonia dissociator system 200, also known as a hydrogen generator, is designed to dissociate ammonia containing 0–5 weight percent dimethylamine along with a similar concentration of trimethyl and monomethyl amines from the UDMH plant. Note that the use of liquid ammonia provides additional safety because the composition is time-averaged. Also note that the trimethyl and monomethyl amines may be present due to impurities in the feedstock or as a result of side reaction in the reactor 44. The ammonia can come as vapors from the second distillation column 78 overhead, or as liquid from the second receiver tank 94. The ammonia vapors can go directly to the DMA dissociator 206. Liquid ammonia must first be vaporized in a steam vaporizer 204 prior to being fed into the DMA dissociator 206.

Input temperature of the vaporized ammonia as it enters the DMA dissociator 206 may range 80°–200°C., with the preferred embodiment operating between 140°–180° C. The DMA dissociator 206 is a fixed bed catalytic reactor utilizing a catalyst such as nickel. Other catalysts, such as iron, cobalt, platinum, palladium, rhodium, ruthenium or other Group 8 metals, and mixtures thereof, as well as the nickel catalyst may be supported on a ceramic support such as alumina or silica, not shown. The output gases from the DMA dissociator 206 are heated by reactor 208 to approximately 1000°–2000° F., with a preferred embodiment of 1300°–1400° F. prior to entering the ammonia dissociator 208. Output gasses from the ammonia dissociator 208 are approximately less than 3% methane, less than 80% hydrogen, and less than 30% nitrogen, by volume. Survival of the methane in the ammonia dissociator 208 is essential to prevent formation of soot or carbon deposits inside the ammonia dissociator 208.

A compressor 212 is utilized to push the dissociated nitrogen/hydrogen into the flow path of the make-up hydrogen prior to mixing with the diluted feedstock at mixing T 36, resulting in complete recycling of the ammonia product within the system. A portion of the compressor 212 effluent is recirculated by means of line x through the DMA dissociator 206 to provide the hydrogen required to convert amines into methane.

Additionally, the gasses withdrawn from the first separation tank 56 may be routed to a scrubber unit 302 via scrubber input line 300. Water from the holding tank 170 is pumped through scrubber input line 308 by pump 310 into the scrubber 302. This water is used to scrub the gasses coming from the first separation tank 56 in order to remove compounds such as ammonia and dimethylamines. Removal of the ammonia and dimethylamines reduce the formation of NOx in the boiler when the gases are burned. The scrubbed gases released from the scrubber 302 are routed through line 306 to an off-gas converter reactor 218. The purpose of this reactor 218 is to convert any remaining feedstock that could still be in this stream. This reactor 218 serves as a guard bed to insure that none of the feedstock is transferred to the boiler (not shown) and burned. Use of the off gases in this manner advantageously reduces the amount of outside fuel required for operation of the boiler, and the use of reactor 218 prevents the forming of toxic nitroamines during boiler operation. The used water from the scrubber 302 is routed through line 304 and input into the first distillation column 62 in order to remover the ammonia, dimethylamines and other basic compounds form this recycled water.

Alternatively, the gases withdrawn from the first separation tank 56 may be routed through an off gas knock out condenser (not shown), where these off gases are cooled to approximately 5° C. The cooling down of the off gases to 5° C. will knock down most of the amines and ammonia, this condensate can be collected in a cold flash separator (not shown) and returned to the first distillation column 62. Any gases remaining in the cold flash separator can be repiped, and therefore recycled, into the hydrogen supply stream.

Persons of ordinary skill in the art will understand that, during the practice of this invention, various systems and apparatus can be employed to monitor and control the rate of flow, temperatures and concentrations of the feed and resultant products. For example, a distributor control system, now shown, and safety interlocks may be included in this invention for continuous monitoring of the equipment in the system, and controlling the system in order to maintain the safety and integrity of the system. If the control system detects a high temperature in reactor 44 that is greater than expected, pumps may be shut down so that energetic material does not continue to flow into the reactor 44.

Interlocks, evident to those skilled in the art from a review of this specification, are provided throughout the system. For example, an interlock is provided on the ratio of recycle fluid, that is, the inert fluid that is being recycled and mixed with the energetic material. The interlock is set such that if the ratio is out of specification, undiluted or under diluted feed material will be prevented from entering the system.

In another embodiment of the invention, a gas chromatography analytical system is integrated into the subject invention for analyzing samples and products throughout the system. The sampling locations are evident to those skilled in the art according to the present invention. For example, the gas chromatography system of the present invention utilizes eight (8) sample streams, the eight streams multiplexed for analysis of the reactor outlet in order to detect undesirable concentrations of feed material. Other analytical systems utilizing various amounts of flow streams may also be employed.

In summary, the chemical plant of the present invention provides novel features for the disposal of hydrazine propellant and other energetic materials. One novel feature is the dissociation of ammonia product for use as a source of hydrogen within the system, thereby reducing operating cost of the system by not requiring additional supplies of hydrogen. Another novel feature is the transfer of heat from the recovered hot water bottoms of the first rectifier for the pre-heating of the diluted feedstock, thereby conserving energy within the system and reducing the need for fuel for the boiler. An additional novel feature is the use of water bottoms from the first distillation column for dilution of the energetic feed material, thereby recycling the water within the system and reducing the need for outside sources of water. A still further novel feature of novelty is the use of a scrubber to scrub the fuel gas stream to remove compounds that could form NOx in the boiler operation, as well as the use of recycled water from the bottoms of the first distillation column to scrub these fuel gases. Another novel feature is the use of excess hydrogen from the ammonia dissociator as fuel for the boiler package, thereby reducing the need for outside sources of fuel to power the system. A further feature of novelty is the use of increased operating pressure in the second distillation column, thereby reducing the operating temperature of the second distillation column and preventing undesirable decomposition of organic materials. Still another feature of novelty is the portability and compactness of the system, such that the system can be broken down and transported to locations where the undesirable source material is located. The closed-loop design allows the system to be used in locations where water and hydrogen are not abundant for the catalytic hydrotreating of energetic materials.

Having thus described the invention in rather full detail, it will be understood that such detail need not be strictly adhered to but that various changes and modifications may suggest themselves to one skilled in the art, all falling within the scope of the present invention as defined by the subjoined claims.

What is claimed is:

1. A system for the catalytic hydrotreating of energetic material, comprising:
   a. a first mixing zone connected to receive the energetic material;
   b. a fluid supply line connected to deliver a carrier fluid to the first mixing zone for dilution of the energetic material;
   c. a second mixing zone connected to receive the diluted energetic material;
   d. a source of hydrogen connected to mix with the diluted energetic material;
   e. a catalytic hydrotreating reactor connected to receive the diluted energetic material mixed with hydrogen for catalytic treatment thereof into a reactor output including amines and ammonia product;
   f. means connected to an output of the reactor for separation of ammonia product from the reactor output;
   g. means connected to an output of the reactor for separation of ammonia product from the reactor output;
   h. means for dissociating the ammonia product into hydrogen, nitrogen and organic materials;
   i. means for recycling the dissociated hydrogen for use as at least part of the hydrogen source; and
   j. a plurality of receiver tanks connected for storage of the separated reactor output.

2. A system for the catalytic hydrotreating of energetic material according to claim 1, wherein the reactor is a co-current down flow trickle bed reactor containing a Group VIII metal catalyst.

3. A system for the catalytic hydrotreating of energetic material according to claim 1, wherein the energetic material is an alkyl hydrazine.

4. A system for the catalytic hydrotreating of energetic materials according to claim 1, wherein the energetic material is a nitrogen-containing explosive.

5. A system for the catalytic hydrotreating of energetic material according to claim 1, wherein the carrier fluid is at least one member of the group consisting of water, hydrocarbons or alcohols.

6. A system for the catalytic hydrotreating of energetic material according to claim 5, wherein the carrier fluid is water.

7. A system for the catalytic hydrotreating of energetic material according to claim 1, wherein the means for dissociation of the ammonia product comprises:
   a. a means for vaporizing the ammonia product;
   b. a catalytic reactor for the dissociation of amines into methane; and
   c. a catalytic reactor for the dissociation of ammonia into hydrogen and nitrogen.

8. A system for the catalytic hydrotreating of energetic material according to claim 7, wherein the catalytic reactor for the dissociation of amines into methane contains a nickel catalyst.

9. A system for the catalytic hydrotreating of energetic material according to claim 7, wherein the catalytic reactor for the dissociation of ammonia into hydrogen and nitrogen contains an alumina and iron catalyst.

10. A system for the catalytic hydrotreating of energetic material according to claim 1, wherein the ammonia product contains less than 20% amines.

11. A system for the catalytic hydrotreating of energetic material according to claim 1, further comprising means for recycling the carrier fluid for use as at least part of the carrier fluid source.

12. A system for the catalytic hydrotreating of energetic material according to claim 1, further comprising means for recycling the carrier fluid for pre-heating the diluted energetic material.

13. A system for the catalytic hydrotreating of energetic material, comprising:
   a. a first mixing zone connected to receive the energetic material;
   b. a fluid supply line connected to deliver a carrier fluid to the first mixing zone for dilution of the energetic material;
   c. a second mixing zone connected to receive the diluted energetic material;
   d. a second mixing zone connected to receive the diluted energetic material;
   e. a catalytic hydrotreating reactor connected to receive the diluted energetic material mixed with hydrogen for catalytic treatment thereof into a reactor output including amines and ammonia product;

f. means connected to an output of the reactor for separation of the reactor output;

g. means for recycling the carrier fluid for use as at least part of the carrier fluid source;

h. means for recycling the carrier fluid for pre-heating the diluted energetic material, and i. a plurality of receiver tanks connected for storage of the separated reactor.

14. A system for the catalytic hydrotreating of energetic material according to claim 13, wherein the reactor is a co-current down flow trickle bed reactor containing a Group VIII metal catalyst.

15. A system for the catalytic hydrotreating of energetic material according to claim 13, wherein the energetic material is an alkyl hydrazine.

16. A system for the catalytic hydrotreating of energetic material according to claim 13, wherein the energetic material is a nitrogen-containing explosive.

17. A system for the catalytic hydrotreating of energetic material according to claim 13, wherein the carrier fluid is at least one member of the group consisting of water, hydrocarbons or alcohols.

18. A system for the catalytic hydrotreating of energetic material according to claim 13, wherein the carrier fluid is water.

19. A system for the catalytic hydrotreating of energetic material according to claim 13, further comprising means for dissociating the ammonia product into hydrogen, nitrogen and organic materials.

20. A system for the catalytic hydrotreating of energetic material according to claim 1, wherein the energetic material is a member selected from the group consisting of hydrazine, monomethyl hydrazine, dimethyl hydrazine and mixtures thereof.

21. A system for the catalytic hydrotreating of energetic material according to claim 13, wherein the energetic material is a member selected from the group consisting of hydrazine, monomethyl hydrazine, dimethyl hydrazine and mixtures thereof.

22. A method for the catalytic hydrotreating of energetic material, comprising:

(a) diluting the energetic material with a carrier fluid;

(b) mixing the diluted energetic material of (a) with hydrogen;

(c) catalytically hydrotreating the energetic material mixture of (b) through a catalytic hydrotreating reactor so as to produce ammonia or ammonia and corresponding amines;

(d) recovering the ammonia or ammonia and the corresponding amines from the product of (c) and optionally returning the carrier fluid to step (a) and optionally returning the unused hydrogen to step (b), and (e) catalytically dissociating the ammonia from (d) to produce hydrogen and nitrogen and optionally returning the hydrogen and nitrogen to step (b).

* * * * *